United States Patent
Ferraro et al.

(10) Patent No.: US 11,433,007 B2
(45) Date of Patent: Sep. 6, 2022

(54) POWDERED COMPOSITIONS BASED ON POLYHYDROXYALKANOATES AND USES THEREOF IN DENTAL PROPHYLAXES

(71) Applicant: BIO-ON S.p.A., San Giorgio di Piano (IT)

(72) Inventors: Antonino Ferraro, San Giorgio di Piano (IT); Paolo Saettone, San Giorgio di Piano (IT); Mauro Comes Franchini, San Giorgio di Piano (IT)

(73) Assignee: BIO-ON S.p.A., San Giorgio di Piano (IT)

( * ) Notice: Subject to any disclaimer, the term of this patent is extended or adjusted under 35 U.S.C. 154(b) by 71 days.

(21) Appl. No.: 17/253,030

(22) PCT Filed: Jun. 24, 2019

(86) PCT No.: PCT/IB2019/055296
§ 371 (c)(1),
(2) Date: Dec. 16, 2020

(87) PCT Pub. No.: WO2020/003091
PCT Pub. Date: Jan. 2, 2020

(65) Prior Publication Data
US 2021/0113436 A1   Apr. 22, 2021

(30) Foreign Application Priority Data

Jun. 27, 2018 (IT) .................. 102018000006721

(51) Int. Cl.
| | |
|---|---|
| *A61K 8/02* | (2006.01) |
| *A61K 8/25* | (2006.01) |
| *A61K 8/34* | (2006.01) |
| *A61K 8/44* | (2006.01) |
| *A61K 8/85* | (2006.01) |
| *A61Q 11/00* | (2006.01) |

(52) U.S. Cl.
CPC ............... *A61K 8/022* (2013.01); *A61K 8/25* (2013.01); *A61K 8/345* (2013.01); *A61K 8/44* (2013.01); *A61K 8/85* (2013.01); *A61Q 11/00* (2013.01); *A61K 2800/28* (2013.01); *A61K 2800/412* (2013.01); *A61K 2800/805* (2013.01)

(58) Field of Classification Search
CPC ................ A61Q 1/12; A61K 8/85; C12P 7/62
USPC .................................................. 424/489, 497
See application file for complete search history.

(56) References Cited

U.S. PATENT DOCUMENTS

| | | |
|---|---|---|
| 6,648,644 B1 | 11/2003 | Flemmig et al. |
| 7,083,411 B2 | 8/2006 | Flemmig et al. |
| 8,968,787 B2 * | 3/2015 | Gittleman ............... C08L 67/04 424/489 |
| 2012/0317736 A1 | 12/2012 | Gonzales et al. |

FOREIGN PATENT DOCUMENTS

| | | |
|---|---|---|
| WO | 2013191903 A1 | 12/2013 |
| WO | 2017176718 A1 | 10/2017 |

OTHER PUBLICATIONS

International Search Report and Written Opinion in corresponding International Application No. PCT/IB2019/055296 dated Oct. 23, 2019, 18 pages.

* cited by examiner

*Primary Examiner* — Walter E Webb
(74) *Attorney, Agent, or Firm* — MH2 Technology Law Group LLP

(57) ABSTRACT

Powdered composition comprising: (a) 100 parts by weight of at least one polyhydroxyalkanoate (PHA) in the form of particles having an average diameter (d50) from 1 μm to 100 μm, preferably from 5 μm to 60 μm; (b) from 0.1 to 10 parts by weight, preferably from 0.5 to 5 parts by weight, of at least one silicate or silica. The powdered composition, having a relatively low abrasivity index and high flowability, can be used in air-polishing without causing excessive abrasion of the enamel and of the root cementum and without causing sticking in the device. Furthermore, the presence of PHA, being a polymer characterized by high biodegradability, makes the powdered composition particularly suitable for use in the oral cavity.

20 Claims, No Drawings

POWDERED COMPOSITIONS BASED ON POLYHYDROXYALKANOATES AND USES THEREOF IN DENTAL PROPHYLAXES

CROSS-REFERENCE TO RELATED APPLICATION(S)

This application is a national stage entry from International Application No. PCT/IB2019/055296, filed on Jun. 24, 2019, in the Receiving Office ("RO/IB") of the international Bureau of the World Intellectual Property Organization ("WIPO"), published as International Publication No. WO 2020/003091 A1 on Jan. 2, 2020, International Application No. PCT/IB2019/055296 claims priority under 35 U.S.C. § 119 from Italian Patent Application No. 102018000006721, filed on Jun. 27, 2018, in the Italian Patent and Trademark Office ("IPTO⇆"). The entire contents of the above-listed applications are incorporated herein by reference.

The present invention relates to a powdered composition based on a polyhydroxyalkanoate and the use thereof in dental prophylaxis. In particular, the present invention relates to a powdered composition based on a polyhydroxyalkanoate and the use thereof in dental prophylaxis through air-polishing.

It is well known that oral hygiene, and in particular oral hygiene related to tartar, is a determining factor in the prevention of diseases of the dental apparatus, such as caries, gingivitis, periodontitis, peri-implantitis, etc.

Tartar is a deposit that forms around the teeth, produced following the synergistic action of bacterial plaque and the accumulation of calcium salts contained in saliva. This accumulation of calcium salts is mainly composed of mineral elements, formed by about 80% of inorganic salts of phosphorus, calcium and sodium and the remaining 20% of different substances. Between the areas of accumulation of salts and the enamel a bacterial plaque retention zone is generated. If the accumulation of salts is not removed, inside the plaque retention zone uncontrolled proliferation of potentially pathogenic micro-organisms develops, with the consequent formation of metabolites toxic for the health of the oral cavity. However, the removal of the accumulation of salts, once it has taken root on the tooth enamel, is not an easy operation to perform, and the use of a simple toothbrush is not sufficient. In fact, this operation is usually performed by a dentist or by a dental hygienist through the use of appropriate mechanical means.

The air-polishing technique was introduced at the end of the 1970s for dental prophylaxis, and its primary aim is the cleaning of teeth through the removal of plaque from the dental enamel and from the root cementum, and the removal of stains on the tooth enamel.

Air-polishing systems use a device equipped with a nozzle for the exit of a jet of compressed air with various types of powders with abrasive particles of different particle sizes added. The type of powder is chosen based on the type of treatment to be performed. Air-polishing devices allow the dispensing of a well controlled jet thanks to the fact that, around the abrasive jet, they generate an annular jet of water that confines the particles and allows the washing of the treated tooth surface.

The parameters to be considered when choosing the type of powder to be used are the hardness, the size and the shape of the particles that constitute the powder itself.

Other important aspects are the fragmentation capacity of the particles, their abrasive power on the enamel and on the dental root cementum and the effect that the residual particles can have on the oral cavity once the air-polishing treatment is finished.

Commonly used powders are sodium bicarbonate, glycine, calcium phosphosilicate, aluminium hydroxide, calcium carbonate and erythriol.

U.S. Pat. Nos. 6,648,644 and 7,083,411 describe the use of powders (silica, amino acids, sugars, organic acids, salts of sugars and organic acids, boron oxide, silanized silica) for the preparation of compounds to be used for air-polishing in which the powders have a density of up to 2.0 $g/cm^3$ and/or an average particle size of the particles that form the powders not higher than 45 μm.

However, the powders known to a person skilled in the art show the disadvantage of having high abrasive power towards the enamel and the dental root cementum, with the consequent sensitization of the tooth and the onset of pain in the treated patient.

A parameter to consider, to evaluate the abrasive power of the powders, is the hardness of the particles, expressed according to the Mohs scale. The hardness values of the tooth enamel and the dentin are, respectively, 5 Mohs and 3 Mohs.

Powders based on sodium bicarbonate have particles having particle sizes from 40 to 120 μm, hardness of 2.5 Mohs and are highly abrasive.

Powders based on glycine have particles having particle sizes from 25 to 65 μm, hardness of 2.0 Mohs and slightly lower abrasive power than that of sodium bicarbonate, but still detrimental.

Powders based on calcium carbonate have particles having particle sizes from 55 to 70 μm, hardness of 3.0 Mohs and are highly abrasive (abrasive power higher than that of glycine and sodium bicarbonate).

Powders based on aluminium hydroxide have particles having particle sizes from 88 to 325 μm, hardness of 4.0 Mohs and are highly abrasive (abrasive power higher than that of sodium bicarbonate).

A further disadvantage of known powders is the incomplete biodegradability of the particles that compose the powders. This aspect is particularly disadvantageous considering the residual particles that remain inside the oral cavity once the air-polishing treatment is finished. If these particles are not totally biodegradable, their persistence inside the oral cavity could cause damage to the health of the treated patient.

A further parameter to be considered when choosing the type of powder to be used for air-polishing is the tendency towards sticking, i.e. the propensity of the particles to form aggregates that obstruct the normal dispensing of the same by the air-polishing device. In fact, it is fundamental for the powder to have a suitable flow index, i.e. the capacity of the powder to flow fluidly through a calibrated hole.

The Applicant therefore has faced the problem of developing powdered compositions to be used with the air-polishing technique that do not have the drawback of generating, on the enamel and/or on the cementum, a significant level of abrasion, without causing sticking phenomena in the air-polishing device that would prevent the correct dispensing thereof.

The Applicant has now found that such problem, and others that will be better illustrated below, can be solved by using as abrasive powder at least one polyhydroxyalkanoate (PHA) in the form of particles having an average diameter (d50) from 1 μm to 100 μm, preferably from 5 μm to 60 μm, in combination with at least one silicate or silica, having the function of an anti-sticking agent.

In the context of the present description and the attached claims, "average particle diameter" refers to, unless otherwise indicated, the diameter d50 (median value), i.e. the value of the diameter below which there is 50% by weight of the particle population (see "A Guidebook to Particle Size Analysis" published by Horiba Instruments Inc.—2016, available at https://www.horiba.com/fileadmin/uploads/Scientific/eMag/PSA/Guidebook/pdf/PSA_Guidebook.pdf). It can be determined through a laser diffraction technique, according to ISO 13320:2009.

In a first aspect, the present invention therefore relates to a powder composition comprising:

(a) 100 parts by weight of at least one polyhydroxyalkanoate (PHA) in the form of particles having an average diameter (d50) from 1 µm to 100 µm, preferably from 5 µm to 60 µm;

(b) from 0.1 to 10 parts by weight, preferably from 0.5 to 5 parts by weight, of at least one silicate or silica.

Within the context of the present description and claims, the quantities of the various components of the composition are expressed, unless otherwise indicated, as parts by weight with respect to 100 parts by weight of PHA particles.

In a second aspect, the present invention relates to a powdered composition as defined above, for use in dental prophylaxis through air-polishing.

As is known, polyhydroxyalkanoates (PHAs) are polymers produced by micro-organisms isolated from natural environments or even by genetically modified micro-organisms, and are characterized by high biodegradability. They are produced and accumulated by various species of bacteria under unfavourable growth conditions and in the presence of a source of excess carbon. PHAs are synthesized and accumulated by about 300 different microbial species, included in more than 90 kinds of Gram-positive and Gram-negative bacteria, such as for example *Bacillus, Rhodococcus, Rhodospirillum, Pseudomonas, Alcaligenes, Azotobacter, Rhizobium*.

In bacterial cells, PHA is stored in the form of microgranules, whose size and number per bacterial cell varies in different species. They appear as refractive inclusions under an electron microscope, with a diameter ranging from 0.2 to 0.7 µm.

For the purposes of the present invention, the PHA obtained from the microbial synthesis in the form of an aqueous suspension is preferably subjected to an atomization (spray drying) process through an atomizer (spray dryer).

As is known, the spray drying process allows a solid in suspension in a liquid medium, usually an aqueous medium, to be transformed into a dry product in the form of particles with a controlled size distribution. Such process generally provides making the liquid suspension pass at high pressure into a distribution ring, which is provided with a plurality of nozzles from which the suspension exits in the form of micro-droplets. Such micro-droplets are hit by a jet of a hot gas (generally air or nitrogen) which causes almost instantaneous evaporation of the liquid, with the formation of the dried particles that are collected on the bottom of the device. Further details are provided for example in the manual "Handbook of Industrial Drying" by Arun S. Mujumdar, CRC Press, 4th Edition (2014).

In this way, it is possible to obtain the PHA in the form of particles having a substantially spherical shape and with an average diameter (d50) of 1 µm to 100 µm, having a low polydispersity. The shape of the particles is preferably determined by means of a scanning electron microscope. The polydispersity of the particle size distribution can be calculated as the "span", i.e. the ratio (d90−d10)/d50, where d90 is the diameter value below which 90% by weight of the particle population is found, d10 is the diameter value below which 10% by weight of the particles population is found, and d50 is the diameter value below which 50% by weight of the particle population is found (median value). Such ratio (span) preferably has a value from 1.0 to 2.0.

As for the PHA, this is preferably a polymer containing repeating units of formula:

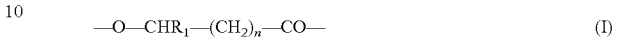

$$-O-CHR_1-(CH_2)_n-CO- \quad (I)$$

where:

$R_1$ is selected from: —H, $C_1$-$C_{12}$ alkyls, $C_4$-$C_{16}$ cycloalkyls, $C_2$-$C_{12}$ alkenyls, optionally substituted with at least one group selected from: halogen (F, Cl, Br), —CN, —OH, —OOH, —OR, —COOR (R=$C_1$-$C_4$ alkyl, benzyl);

n is zero or an integer from 1 to 6, preferably 1 or 2.

Preferably, $R_1$ is methyl or ethyl, and n is 1 or 2.

The PHAs can either be homopolymers, copolymers or terpolymers. In the case of copolymers or terpolymers, they can consist of different repeating units of formula (I), or of at least one repeating unit of formula (I) in combination with at least one repeating unit deriving from comonomers that are able to copolymerize with hydroxyalkanoates, such as lactones or lactams. In the latter case, the repeating units of formula (I) are present in an amount equal to at least 10% in moles with respect to the total moles of repeating units.

Particularly preferred repeating units of formula (I) are those deriving from: 3-hydroxybutyrate, 3-hydroxyvalerate, 3-hydroxyhexanate, 3-hydroxyoctanoate, 3-hydroxyundec-10-enoate, 4-hydroxyvalerate.

Particularly preferred PHAs are: polyhydroxybutyrate (PHB), poly-3-hydroxyvalerate (PHV), poly-3-hydroxyhexanate (PHH), poly-3-hydroxyoctanoate (PHO), poly(3-hydroxybutyrate-co-3-hydroxyvalerate) (PHBV), poly(3-hydroxybutyrate-co-3-hydroxyhexanoate) (PHBH), poly(3-hydroxybutyrate-co-4-hydroxybutyrate), poly(3-hydroxyoctanoate-co-3-hydroxyundecen-10-enoate) (PHOU), poly(3-hydroxybutyrate-co-3-hydroxyvalerate-4-hydroxyvalerate) (PHBVV), polyhydroxybutyrate-hydroxyvalerate copolymer, or mixtures thereof.

According to the aims of the present invention, particularly preferred PHAs are selected from: polyhydroxybutyrate (PHB), polyhydroxybutyrate-hydroxyvalerate copolymer or a mixture thereof.

Preferably, the at least one silica with anti-aggregation action is selected from: pyrogenic silica, colloidal silica.

Preferably, the at least one silicate with anti-aggregation action is selected from: phyllosilicates, e.g. talc or bentonite; hydroxysilicates, e.g. kaolin.

Preferably, the at least one silicate or silica is in form of particles having an average diameter (d50) from 1 µm to 50 µm, preferably from 2 µm to 20 µm.

Preferably, the at least one silica is a hydrophobic silica. These are products that are well known in the art in which the silica is surface treated with a hydrophobing agent, in particular a compound able to react with the hydroxyl groups of the silica so as to make them hydrophobic. Hydrophobing agents most commonly used are for example: hexamethyldisilazane, octyltrialkoxysilane, 1,1,1-trimethyl-N-(trimethylsilyl) silanamine, and others.

For the purpose of regulating the powder density, the composition according to the present invention may comprise a further component selected from: calcium phosphate, for example hydroxyapatite, fluoroapatite, tricalcium phosphate, calcium hydrogen phosphate; calcium carbonate or calcium bicarbonate; fluorinated salts, for example sodium fluoride, sodium monofluorophosphate, stannous fluoride; or mixtures thereof. The quantity of such further component can vary within wide limits, preferably from 5 to 90 parts by weight, more preferably from 10 to 70 parts by weight.

According to a preferred embodiment of the present invention, the powdered composition further comprises from 0.1 to 10 parts by weight, preferably from 0.5 to 5 parts by weight, of at least one sulfate of a metal selected from: alkali metals, alkaline earth metals, aluminium. It is believed that the sulfate also exerts an anti-aggregation action. Preferably, the at least one sulfate is selected from: sodium sulfate, magnesium sulfate, potassium sulfate, aluminium sulfate.

The presence of at least one silica or silicate, and possibly of at least one sulfate, as described above, advantageously allows the flow index of the powdered composition to be increased.

The flow index can be determined through the "flow through an orifice" method described in chapter 2.9.36 of the European Pharmacopoeia (IX Edition of 1 Jan. 2017).

Preferably, the powdered composition of the invention has a flow index, measured with the above "flow through an orifice" method, less than or equal to 20.

According to a preferred embodiment of the present invention, the powdered composition further comprises preferably from 0.1 to 5 parts by weight of at least one flavouring. Preferably said flavouring is a flavouring of natural or synthetic origin and has the aim of imparting to the composition a pleasant taste for the patient.

The powdered composition according to the present invention may possibly further include an abrasive component for air-polishing known in the art, such as, for example: sodium bicarbonate, glycine, erythritol. The quantity of such additional abrasive powder can preferably vary from 1 to 50 parts by weight, more preferably from 5 to 30 parts by weight.

Preferably the powdered composition according to the present invention may include other adjuvant additives, such as hemostatic agents, antimicrobial agents, bleaching agents, soothing agents, gum revitalizers, dyes.

The use of a hemostatic agent can be advantageous for reducing any bleeding of gums during the air-polishing treatment. Preferably, the hemostatic substance can be selected from: potassium alum, aluminium sulfate, aluminium chloride, aluminium hydrochloride, aluminium acetate, ferric sulfate, silver nitrate, vitamin K.

The use of a colouring substance can be advantageous for verifying, through a simple visual inspection, that the powdered composition has been substantially completely removed from the oral cavity at the end of the air-polishing treatment. The colouring substance may preferably be selected from organic dyes or inorganic pigments, preferably for edible use.

The use of a bleaching substance, preferably with chemical action, can be advantageous as it increases the mechanical whitening action intrinsic to the air-polishing technique. The whitening substance can preferably be selected from: carbamide peroxide, sodium perborate, calcium oxide.

The use of an antimicrobial substance can be advantageous for substantially reducing the presence of bacteria in the oral cavity. The antimicrobial substance can preferably be selected from: chlorhexidine, hexetidine, triclosan, stannous chloride, histatin, phenol, zinc ion, silver ion, iodine, dodecylamine, bipyridine, tannic acid derivative, amphiphilic lipid, quaternary ammonium salt, phosphonium fluoride salt, benzoic acid, salicylic acid.

The use of a soothing substance can be advantageous for reducing inflammations and gum irritations. The soothing substance can preferably be selected from: bisabolol, glycyrrhetinic acid, hypericin, panthenol.

The use of a gum revitalizing substance can be advantageous to promote renewal of the gum cells and to give vigour and vitality to the cells. The gum revitalizing substance may preferably be selected from: vitamin E, aloe vera extract, vitamin B5, allantoin.

As described above, the powdered PHA is preferably obtained from an aqueous solution of PHA, which is subjected to an atomization (spray drying) process. The spray-drying process can be performed in a spray dryer according to known techniques, using a flow of gas (generally air or nitrogen) having an inlet temperature from 50° C. to 250° C. and an outlet temperature from 40° C. to 150° C. Preferably the aqueous suspension of PHA, possibly premixed with the other components of the composition, is nebulized inside the chamber in which the atomization (spray-drying) takes place, through a "bi-fluid" type nozzle, or the nebulization takes place through a pressure mechanism, or through a rotating mechanism, or through ultrasound.

The following embodiment examples are provided merely to illustrate the present invention and should not be construed in a sense that would limit the scope of protection defined by the claims.

EXAMPLE 1

A powdered composition was prepared as outlined in Table 1:

TABLE 1

| Component | % (w/w) | parts by weight |
|---|---|---|
| polyhydroxybutyrate (PHB) | 60 | 100 |
| hydroxyapatite | 38 | 63.3 |
| natural orange flavouring | 1.5 | 2.5 |
| hydrophobic pyrogenic silica | 0.5 | 0.8 |

The PHB was in the powder form obtained through spray drying an aqueous suspension of PHB.

Through a laser diffraction particle size analyzer (Mastersizer 3000 by Malvern), equipped with a wet dispersion unit, the particle size of the PHB was determined after spray-drying. For that purpose, increasing quantities of the powdered PHB were dispersed in water, until a laser obscuration value of about 10% was reached. The average particle diameter, expressed as d50, was equal to 30 μm, while the polydispersity index (span) was equal to 1.90.

The pyrogenic silica was made hydrophobic through treatment with 1,1,1-trimethyl-N-(trimethylsilyl) silanamine, and had a surface area (BET) equal to 230-290 m$^2$/g.

Flow Index.

The flow index of the above powdered composition was evaluated.

The flow index was determined through the "flow through an orifice" method described in chapter 2.9.36 of the European Pharmacopoeia (IX Edition of 1 Jan. 2017), using the "Powder Flowability Test Model BEP2" instrument.

In particular, 50 g of powdered composition were placed in a hollow cylinder closed, in the lower portion, by a disc provided with an orifice of a known diameter. A collecting beaker was placed below the cylinder in proximity to the orifice. The test is positive when the powdered composition flow from the orifice leaving it clearly visible to an observer located above the cylinder. The test was sequentially repeated with discs provided with an orifice of a gradually smaller diameter. The value of the flow index coincides with the diameter (expressed in mm) of the smallest orifice with which the test result was positive.

For the above composition a flow index of 18 was determined.

Transport Speed.

For the above powdered composition, the transport speed in an air-polishing device ("Combi touch" apparatus made by Mectron SpA) was evaluated. The powdered composition was made to flow through the device, in the absence of water, for about 1 minute. The jet of powder and air was conveyed into a collecting beaker full of water, in order to collect all of the powdered composition that flows through the device.

Thus a transport speed of 2.30 g/min was measured.

Abrasivity Index.

For the above powdered composition the abrasivity index of the dentin was evaluated.

The test was performed in vitro on recently extracted bovine teeth. After extraction the teeth were washed by rinsing with deionized water. Subsequently the surface of the tooth root was smoothed through treatment with abrasive paper. The teeth thus treated were fixed to a support and covered with a film only leaving a strip 2 mm wide uncovered at the tooth root. At this point the zone without film was treated with the air-polishing technique using the above powdered composition in an air-polishing device ("Combi touch" device made by Mectron SpA). The air-polishing treatment was performed for 10 seconds at a jet pressure of 4 bar and at a distance of 4 mm from the tooth root to the device.

After the air-polishing treatment was completed, the abrasivity index was evaluated, i.e. the loss of dentin through a Hirox 3D digital microscope.

The evaluation was performed by marking out 5 depth profiles perpendicular to the plane on which the 2 mm wide strip lies and calculating the average of the 5 depth measurements of the defects created following the air-polishing treatment. The average value of the depth measurements was expressed in μm and corresponds to the abrasivity index of the powdered composition used for performing the air-polishing treatment.

For the above composition of Example 1 an abrasivity index of 1.5 μm was determined.

From the results obtained it is therefore possible to state that the powdered composition according to the present invention has a sufficient abrasivity index for the removal of plaque but however relatively low, therefore it does not cause any excessive abrasion of the enamel or the root cementum. Furthermore, the presence of PHA, being a polymer characterized by high biodegradability and biocompatibility, makes the powdered composition particularly suitable for use in the oral cavity. Furthermore, the flow index and transport speed measurements demonstrate that the composition can be effectively used in an air-polishing device, without causing any sticking or flow irregularities.

EXAMPLE 2

A powdered composition as reported in Table 2 was prepared:

TABLE 2

| Component | % (w/w) | parts by weight |
|---|---|---|
| polyhydroxybutyrate (PHB) | 81.5 | 100 |
| sodium bicarbonate | 15 | 18.4 |
| natural orange flavouring | 2.5 | 3.1 |
| hydrophobic pyrogenic silica | 1 | 1.2 |

The PHB, hydrophobic pyrogenic silica and sodium bicarbonate were the same ones used in Example 1. The average particle diameter (d50) was equal to 40 μm and the polydispersity index (span) was equal to 2.00.

The invevntion claimed is:

1. A powdered composition, comprising:
   (a) 100 parts by weight of at least one polyhydroxyalkanoate (PHA) in a form of particles having an average diameter (d50) greater than or equal to 1 micron (μm) and less than or equal to 100 μm: and
   (b) greater than or equal to 0.1 parts by weight and less than or equal to 10 parts by weight of at least one silicate or at least one silica.

2. The powdered composition of claim 1, wherein the at least one PHA is in the fou ii of particles having substantially spherical shape and a polydispersity index (span) greater than or equal to 1.0 and less than or equal to 2,
   where the span is a ratio (d90-d10)/d50,
   where d90 is a diameter value below which 90% by weight of a population of the particles is found,
   where d10 is the diameter value below which 10% by weight of the population of the particles is found, and
   where d50 is the diameter value below which 50% by weight of the particle population of the particles is found (median value).

3. The powdered composition of claim 1, wherein the at least one PHA is selected from: polyhydroxybutyrate (PHIS), polyhydroxybutyrate-hydroxyvalerate copolymer, or a mixture thereof.

4. The powdered composition of claim 1, wherein the at least one silica is selected from: pyrogenic silica or colloidal silica.

5. The powdered composition of claim 1, wherein the at least one silicate is selected from:
   phyllosilicatesor or hydroxysilicates.

6. The powdered composition of claim 1, wherein the at least one silicate or the at least one silica is in a form of particles having an average diameter (d50) greater than or equal to 1 in and less than or equal to 50 μm.

7. The powdered composition of claim 1, wherein the at least one silica comprises hydrophobic silica.

8. The powdered composition of claim 1, further comprising an additional component selected from:
   calcium phosphate, calcium carbonate, calcium bicarbonate, fluorinated salts, or mixtures thereof.

9. The powdered composition of claim 8, wherein the additional component is present in an amount greater than or equal to 5 parts by weight and less than or equal to 90 parts by weight.

10. The powdered composition of claim 1, further comprising:
    greater than or equal to 0.1 parts by weight and less than or equal to 10 parts by weight of at least one sulfate of metal selected from: alkali metals, alkaline earth metals, or aluminum.

11. The powdered composition of claim 1, having a flow index, determined by the "flow through an orifice" method described in chapter 2.9.36 of the European Pharmacopoeia (IX Edition of 1 Jan. 2017), less than or equal to 20.

12. The powdered composition of claim 1, further comprising:
greater than or equal to 0.1 parts by weight and less than or equal to 5 parts by weight of at least one flavoring.

13. The powdered composition of claim 1, further comprising:
an additional abrasive component selected from: sodium bicarbonate, glycine, or erythritol, in an amount greater than or equal to 1 part by weight and less than or equal to 50 parts by weight.

14. The powdered composition of claim 1, further comprising:
at least one adjuvant additive selected from: hemostatic agents, antimicrobial agents, bleaching agents, soothing agents, gum revitalizers, or dyes.

15. The powdered composition of claim 1, wherein the at least one PHA in the form of particles is obtained from aqueous suspension of the at least one PHA using an atomization (spray drying) process.

16. A method of dental prophylaxis, the method comprising: air-polishing teeth using the powdered composition of claim 1.

17. The method of claim 16, wherein the teeth are human teeth.

18. The method of claim 16, wherein the teeth are other than human teeth.

19. A powdered composition, comprising:
(a) 100 parts by weight of at least one polyhydroxyalkanoate (PHA) in a form of particles having an average diameter (d50) greater than or equal to 5 microns (μm) and less than or equal to 60 μm; and
(b) greater than or equal to 0.1 parts by weight and less than or equal to 10 parts by weight of at least one silicate or at least one silica.

20. A powdered composition, comprising:
(a) 100 parts by weight of at least one polyhydroxyalkanoate (PEIA) in a form of particles having an average diameter (d50) greater than or equal to 1 micron (μm) and less than or equal to 100 μm; and
(b) greater than or equal to 0.5 parts by weight and less than or equal to 5 parts by weight of at least one silicate or at least one silica.

* * * * *